United States Patent [19]

Terrell et al.

[11] 4,346,246

[45] Aug. 24, 1982

[54] PROCESS FOR ADJUSTING THE HALOGEN CONTENT OF HALOGENATED ALIPHATIC ETHERS

[75] Inventors: Ross C. Terrell, Clark; Kirsten Hansen, Berkeley Heights, both of N.J.

[73] Assignee: Airco, Inc., Montvale, N.J.

[21] Appl. No.: 149,360

[22] Filed: May 13, 1980

Related U.S. Application Data

[63] Continuation of Ser. No. 19,953, Mar. 12, 1979, abandoned.

[51] Int. Cl.$^3$ .................. C07C 41/01; C07C 41/24
[52] U.S. Cl. .................. 568/684; 568/683
[58] Field of Search .................. 568/683, 684

[56] References Cited

U.S. PATENT DOCUMENTS 4,149,018 6/1979 Bell et al. .................. 568/684

*Primary Examiner*—Howard T. Mars
*Attorney, Agent, or Firm*—Roger M. Rathbun; Larry R. Cassett

[57] ABSTRACT

Process for adjusting the halogen content of halogenated aliphatic ethers, by selective replacement of a halide substituent on the ether with a hydrogen. The process is particularly useful for the production of certain inhalant anesthetics.

9 Claims, No Drawings

PROCESS FOR ADJUSTING THE HALOGEN CONTENT OF HALOGENATED ALIPHATIC ETHERS

This is a continuation of application Ser. No. 19,953, filed Mar. 12, 1979, now abandoned.

INTRODUCTION

This invention relates to processes for adjusting the halogen content of halogenated aliphatic ethers, by selective reduction, i.e., replacement of a halide substituent on the ether with a hydrogen. More specifically, the invention is concerned with new processes, and with improvements in existing processes, for the production of certain halogenated aliphatic ethers that are useful as inhalant anesthetics.

BACKGROUND

The halogenated ether, 1,1,2-trifluoro-2-chloroethyl difluoromethyl ether, $CHF_2OCF_2CHFCl$, is a valuable inhalant anesthetic, enflurane, made and sold under the trademark ETHRANE by Airco, Inc., Montvale, N.J. 07645. It is referred to hereafter as enflurane.

The presently-employed process for manufacturing this anesthetic material generates a number of by-product streams, each characterized by having more chlorine in the molecule than does the desired anesthetic product. One such by-product stream contains the compound of $CF_2HOCF_2CFCl_2$, which is very difficult to remove from the desired product by distillation or other separating technique, and of course it represents a yield loss for the presently-employed process.

Other by-product streams are produced in the presently-employed process as "bottoms" from the vacuum stills. These bottoms contain the following components in varying proportions:

$CH_2ClOCF_2CHFCl$
$CCl_3OCF_2CHFCl$
$CCl_2HOCF_2CHFCl$
$CCl_2HOCF_2CFCl_2$
$CClH_2OCF_2CFCl_2$
$CCl_3OCF_2CFCl_2$

At the present time, these materials are useless by-products that reduce the efficiency of the currently-employed process.

Another important halogenated ether anesthetic is 1-chloro-2-trifluoro difluoromethyl ether, $CF_3CHClOCHF_2$, isoflurane, made and sold under the trademark FORANE by Airco, Inc. It is referred to hereafter as isoflurane. In the process for manufacturing this anesthetic, care must be exercised to avoid by-product formation, and the process now in use achieves low conversions to the desired product. Representative by-products produced include $CF_3CCl_2OCHF_2$, which has been considered to be useless in the past.

The selective reduction of halogenated aliphatic ethers is extremely difficult to accomplish because of the different responses exhibited by ethers of this kind to a given reactant or to given reactants. Thus, there are three important reactions that halogenated aliphatic ethers may undergo in the presence of a base.

First, a hydrolysis or nucleophilic displacement reaction may occur. This is a reaction in which the halogen atom is replaced by OH, OR, or other nucleophilic group, as represented by the equation:

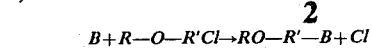

where B is OH or OR.

Second, dehydrohalogenation may occur. In this reaction, hydrogen and halogen are removed from adjacent carbon atoms to form a double bond:

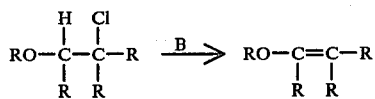

This type of reaction is described in U.S. Pat. No. 2,803,666, where this reaction occurs:

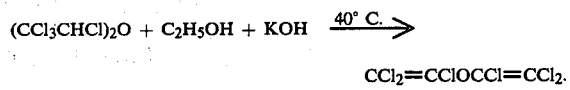

$$CCl_2=CClOCCl=CCl_2.$$

It is also described by Corley et al. in 78 JACS 3489 at 3491 and 3492, as for example in this preparation:

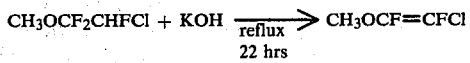

Third, selective reduction may take place, in accordance with the present invention. In this reaction the halogen is replaced by hydrogen, as in the examples of this application.

In order for the reduction reaction to work, the ether must not undergo a hydrolysis or nucleophilic displacement reaction or dehydrohalogenation reaction, which is faster than the reduction. In addition, any ether formed by the reduction reaction must not undergo further reactions, especially dehydrohalogenation.

In order for selective reduction to take place, rather than hydrolysis or nucleophilic displacement or dehydrohalogenation, certain conditions must be met. The reactions of the halogenated ethers have been little explored and have been considered highly unpredictable. The present invention is remarkable in that only certain halogenated ethers can be selectively reduced, and in that the reduction is selective.

SUMMARY OF THE INVENTION

It has now been discovered that selective replacement of a chlorine or bromine substituent on certain halogenated aliphatic ethers, with hydrogen, can be accomplished by reacting one of the certain substituted ethers with an alkanol and a base, preferably but not necessarily in the presence of a catalyst. The halogen replaced may be bonded to a terminal carbon or to an inner carbon.

The process of the invention can be concisely described as a process for replacing a halogen substituent with hydrogen in a halogenated aliphatic ether of the methyl-ethyl or ethyl-ethyl type, comprising reacting with a primary or secondary alkanol and an inorganic base a halogenated aliphatic ether of the formula:

(a) $CX_3OCY_2CZ_3$ where
$CX_3$ is $CF_3$, $CH_3$, $CH_2F$, $CF_2CL$, $CF_2Br$, or $CHF_2$; and
$CZ_3CY_2$ is $CF_3CCL_2$, $CF_3CClBr$, $CF_3CBr_2$, $CFCl_2CF_2$, $CFCl_2CFCl$, $CFCl_2CFBr$, $CFBrClCF_2$, $CFClBrCFCl$, $CFBrClCFBr$, CCl$_3$CF$_2$, CFBr$_2$CF$_2$, CFBr$_2$CFCl, CFBr$_2$CFBr, CCl$_2$BrCF$_2$, CClBr$_2$CF$_2$ or CBr$_3$CF$_2$ or (b) CX$_3$CY$_2$OCY$_2$CX$_3$ where at least one of the CX$_3$CY$_2$ groups is selected from the following:
CF$_3$CCl$_2$, CF$_3$CClBr, CF$_3$CBr$_2$, CFCl$_2$CF$_2$, CFCl$_2$CFCl, CFCl$_2$CFBr, CFBrClCF$_2$, CFBrClCFCl, CFBrClCFBr, CCl$_3$CF$_2$, CFBr$_2$CF$_2$, CFBr$_2$CFCl, CFBr$_2$CFBr, CCl$_2$BrCF$_2$, CClBr$_2$CF$_2$ or CBr$_3$CF$_2$;

and the other CX$_3$CY$_2$ group may be the same or may be selected from the following:
CF$_3$CH$_2$, CF$_3$CHF, CF$_3$CHCl, CF$_3$CHBr, CF$_3$CF$_2$, CF$_3$CFCl, CF$_3$CFBr, CH$_3$CH$_2$, CHFCH$_2$, CHF$_2$CF$_2$, CFClCF$_2$, CF$_2$ClCFCl, CF$_2$ClCFBr, CF$_2$BrCF$_2$, CF$_2$BrCFCl, CF$_2$BrCFBr, CHFBrCF$_2$, CHCl$_2$CF$_2$, CHClBrCF$_2$ or CHBr$_2$CF$_2$.

THE PRIOR ART

No prior art is known that discloses or suggest the present process.

In *Fluorine Chemistry Reviews*, by Metille and Burton, p. 354, the authors describe the dehalogenation of CF$_3$I to CF$_3$H, using KOH in a solvent of high dielectric constant, specifically referring to ethanol. The use of the reaction to dehalogenate CF$_3$CF$_2$I to CF$_3$CF$_2$H is also discussed.

The source article referred to by Metille and Burton is Banus et al., J. Chem. Soc. 1951, pp. 60–64. This publication states that it is known that the C-I bond in CF$_3$I can undergo homolytic fission but that, apart from decomposition, CF$_3$Cl, CF$_2$Cl$_2$ and CHF$_2$Cl "do not show reactions involving the homolytic or heterolytic fission of the carbon-chlorine bond." The publication in general stresses that the iodo compounds are unique as compared to the corresponding bromo or chloro compounds. It would not, therefore, suggest the use of the same type of reaction even for brominated, chlorinated, or fluorinated alkanes, let alone ethers.

Young, U.S. Pat. No. 3,391,204, in his Example 11, describes the reaction:

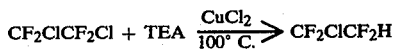

where TEA represents triethanolamine.

Examples 12 and 13 describe generally similar dehalogenations. Young says that alcohol may be present, but characterizes the alcohol as an "inert" solvent, and his reaction did not operate on ethers, but rather on halogenated alkanes.

In German Pat. No. 2,554,884, partial dechlorination of F$_2$CHOCFClCF$_2$Cl, an ether, was accomplished by the use of hydrogen and a catalyst of either palladium or a complex metallic hydride.

Some reactions involving halogenated alkanes are to be found in the literature. U.S. Pat. Nos. 3,527,813 and 3,535,388 describe the introduction of chlorine and of fluorine into halogenated alkanes.

DETAILED DESCRIPTION OF THE INVENTION

The present invention involves the discovery that when a halogenated aliphatic ether initial compound, selected from a limited class of halogenated ethers as defined above, is reacted with an alkanol and a base, one chlorine or one bromine is selectively replaced with hydrogen. This is a rather remarkable reaction because it occurs despite the presence on the same molecule of —CF$_3$ or

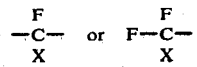

groups, where X is chlorine or bromine. It is also a very valuable reaction because it is specific and permits the conversion of previously useless by-products to valuable products, and also offers a new tool for synthesis.

The two primary areas of immediate commercial interest relate to the preparation of the two inhalant anesthetics mentioned above, as follows.

Preparation of Enflurane Anesthetic, CHF$_2$OCF$_2$CHFCl

The halogenated ether CF$_2$HOCF$_2$CFCl$_2$ is a particularly undesirable by-product of the presently-employed process for the preparation of enflurane anesthetic. It is readily reduced to enflurane in good yield by the process of the present invention, as follows:

(I)

(enflurane anesthetic)

Using this reaction, a product stream from the presently-employed process for producing enflurane, that contains this by-product I, can be upgraded by reacting the product stream itself to convert the by-product I to enflurane, in situ. The enflurane itself, that is present in the product stream, is not affected by the reaction.

In addition, the other halogenated ether by-products mentioned above, that are produced as "bottoms," can be further processed by distillation and chlorination to obtain a mixture containing a high proportion of the ether CHCl$_2$OCF$_2$CFCl$_2$. Fluorination of this ether leads to I above, which can then be reacted in accordance with the invention to produce more enflurane, thus materially improving overall process yield and economics.

It should be noted that when the alkanol employed is methanol, 1.5 moles are required per mole of ether, so that the equations above and below, that employ methanol, are not balanced. The reason is that methanol undergoes the Cannizzaro reaction. When other suitable alkanols are employed which do not give a Cannizzaro reaction, the reaction requires one mole of the alkanol to one mole of reactant ether.

Preparation of Isoflurane Anesthetic, CF$_3$CHClOCHF$_2$

In the isoflurane manufacturing process, CF$_3$CH$_2$OCHF$_2$ is chlorinated to give CF$_3$CHClOCHF$_2$, isoflurane. However, the chlorination must be done at low conversions in order to avoid formation of large amounts of the by-product CF$_3$CCl$_2$OCHF$_2$. However, this by-product can now be reduced to isoflurane as follows:

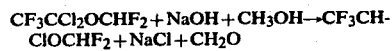

GENERAL

Only a limited number of halogenated ethers are susceptible to selective reduction in accordance with the invention.

As to those of the formula $CX_3OCY_2CZ_3$, as defined above, those ethers that are suitable for use in the present invention were selected from a very large number of halogenated ethers of the methyl-ethyl type, based upon several rules. These rules eliminate those halogenated methyl-ethyl type ethers that would not be suitable by reason of side reactions, either initially or after reduction. These rules are:

1. No $OCY_2CZ_3$ group can have the configuration $O$—$CH$—$CX'$ where $X'$ is Br or Cl, since these compounds would probably eliminate $HX'$ to give $-O-C\!=\!C$ in the presence of base. ($CF_3OCHFCF_2Br$ and $CF_3OCHFCF_2Cl$ may be exceptions to this rule, but are not within the scope of the invention).
2. No $OCY_2CZ_3$ group shall have more than one hydrogen on the $\beta$ carbon unless $CY_2$ is $CH_2$ or $CF_2$; i.e. where two of the $Z=H$, then $CY_2$ must be $CH_2$ or $CF_2$. Otherwise the halogenated ether compounds would not only be unstable to base but some of them would decompose spontaneously.
3. Within the $OCY_2CZ_3$ group, there must be either two chlorines, two bromines, or one bromine and one chlorine on one of the carbon atoms, otherwise the compound will not be reduced.

The first two rules eliminate those halogenated ethers that are unstable in the reaction mixture of this invention. The third rule confines those ethers that have survived the screening by rules 1 and 2 to those that would be reduced, and in addition, eliminates reduced compounds that would not be stable in the presence of the base in the reaction mixture. The application of these rules, of course, severely limits the number of halogenated ethers that are available for use in the selective reduction process of the invention.

The same considerations can be applied in identifying those halogenated ethers of the ethyl-ethyl type that are suitable for use in practising the invention.

The alkanol reactant is a primary or secondary alcohol, preferably a 1 to 4 carbon alkanol (i.e., a lower alkanol), but alkanols of any known chain length up to about 12 carbons are useful and can be expected to be effective, although even higher alcohols are operative. Water soluble alcohols are preferred. The alkanol may be substituted but preferably is not, as a matter of economics. While methanol and ethanol are generally preferred because of availability and cost, isopropanol and sec-butanol are useful and also are readily available.

The base may be: an alkali metal dissolved in the alkanol; an alkali metal or alkaline earth metal hydroxide, dry or in aqueous or alcoholic solution; or any strongly basic material that does not interfere with the desired reaction. Sodium hydroxide, sodium methylate, potassium hydroxide, lithium hydroxide and calcium hydroxide, are examples of suitable basic materials. Ammonia and sodium carbonate are useful in many reactions.

Catalysts are generally not essential but are useful for many individual reactions in improving reactions rates, yields or both. The catalyst, in finely divided or other suitable state, may be a metal-containing (advantageously, in most cases, a varivalent metal-containing) catalyst, more particularly, a copper-containing catalyst such as metallic (elementary) copper or a copper salt of an inorganic or organic acid, e.g., copper chloride, bromide, nitrate, acetate, propionate, etc.; or corresponding salts of silver, cobalt, tin, manganese, nickel, iron, molybdenum, chromium, antimony, vanadium and the like, or the said varivalent metals in elementary form, or alloys thereof with each other or with other metals. Preferably a copper-containing catalyst, specifically elementary copper in powder form, or a copper salt, is employed. In general, the use of a catalyst comprising, for example, one or more of the metals identified above, or the inorganic or organic salts thereof, tends to produce higher conversions, shorter induction periods, and lower operating temperatures.

Preferred catalysts include not only the finely divided metals, metal salts, but also the amines, the mixtures thereof with metal powders and metal salts. The most preferred catalysts are mixtures of copper chloride with triethanolamine. Other suitable amines that may be used, depending on the particular reaction, include:

| | |
|---|---|
| Methylamine(monomethylamine) | Hexamethylenetetramine |
| Dimethylamine | Ammonium chloride |
| Diethylamine | Benzyl trimethyl ammonium methoxide |
| Triethylamine | |
| Isopropylamine | Ethylene diamine |
| Di-n-propylamine | Triethylene tetramine |
| Piperidine | N,N,N-trimethyl ethylene diamine |
| Morpholine | |
| Monoethanolamine | N,N-diethylene diamine |
| Diethanolamine | 1,2-cyclohexylene dinitrilo acetic acid |
| Hydrazine | |
| Aniline | 3-dimethylamino propylamine |
| Pyridine | Ethylenediamine tetraacetic acid |
| | Diazo bicyclo (2,2,2) octane |
| | N-(2-amino ethyl morpholine) |

CONDITIONS OF REACTION

The alkanol and base should be employed in excess over the theoretical amount required to effect the desired reduction of the ether. The alkanol may function both as a reactant and solvent and may be present in substantial excess for that reason. The limits are those established by the practical considerations of reaction kinetics, ease of recovery of the product, and conservation of energy.

The temperature of the reaction is dependent upon the particular reactants employed and may range, for example, from about 0° C. to about 100°–120° C. or higher and, preferably, from about 20° C. to about 80° C. The temperature and/or pressure advantageously are such that the reaction mass is in a liquid state during the course of the reaction. The reaction is exothermic, and once initiated, may require cooling, depending upon the equipment available and other conditions.

The time of the reaction is not important since one may prefer to carry out the reaction for a relatively short period of time with a relatively low conversion rate, rather than to make the reaction go substantially to completion. In general, the time of the reaction depends upon the particular reactants employed, the temperature of the reaction, the efficacy of the catalyst or catalyst system (if employed), and other infuencing factors. Generally, just a few hours up to about thirty, is adequate to produce a suitable yield.

The pressure used is dependent primarily upon the particular reactants employed. The reaction may be carried out at atmospheric pressure. The pressure employed seems to have no material effect on the course of the reaction.

The product may be isolated by any suitable means from the reaction mass. Ordinarily, the product is insoluble and is precipitated by a water-wash, which removes any water-soluble reaction products and by-products.

To explain the invention further, several demonstrations of it are reported in the following examples. All temperatures are in °C., and all parts and percentages by weight, as is, unless expressly stated to be otherwise.

EXAMPLE 1

Production of Isoflurane Anesthetic

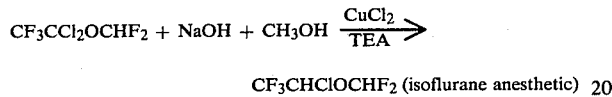

$CF_3CHClOCHF_2$ (isoflurane anesthetic)

A mixture of $CF_3CCl_2OCHCl_2$ (44 g, 0.2 mole), 50% aqueous sodium hydroxide solution (20 g, 0.25 mole), methanol (100 ml), $CuCl_2$ (1 g), and triethanolamine (1 g), was refluxed for five hours and poured into water. The water-insoluble layer was analyzed by gas chromatography and found to contain 16% unreacted $CF_3CCl_2OCHF_2$, 25% methanol, and 54% $CF_3CHClOCHF_2$ (isoflurane anesthetic).

EXAMPLE 2

Different Reactant Ether, With Catalysts

Example 2A

Production of Enflurane

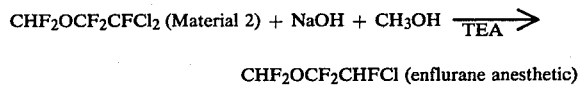

$CHF_2OCF_2CHFCl$ (enflurane anesthetic)

A mixture of $CHF_2OCF_2CHCl_2$ (44 g, 0.2 mole), 50% aqueous sodium hydroxide (20 g, 0.25 mole) methanol (100 ml), $CuCl_2$ (1 g), and triethanolamine (1 g), was refluxed for seven hours and then poured into water. The water-insoluble product recovered (34 g) was analyzed by gas chromatography and found to be 77% unreacted $CHF_2OCF_2CFCl_2$ (Material 2) and 18% $CHF_2OCF_2CHFCl$ (enflurane).

Material 2 can be separated as a "bottom" in a still from the enflurane product, for recycling through the process. The enflurane distillate, in purified form, is useful as an inhalant anesthetic.

Example 2B

Purification of Enflurane

A reaction product containing enflurane together with about 5% of Material 2 was purified as follows.

A mixture of $CHF_2OCF_2CHFCl$ (95.6 g) and $CHF_2OCF_2CFCl_2$ (4.4 g), methanol (15 ml), copper (1 g), ethanolamine (6 g), and sodium hydroxide pellets (8 g), was refluxed for five hours and then washed with water. The water insoluble product (88.9 g) was shown by gas chromatography to be 99.7% pure $CHF_2OCF_2CHFCl$, with no $CHF_2OCF_2CFCl_2$ present.

Example 2C

Enflurane Preparation with a Catalyst System

A mixture of $CHF_2OCF_2CFCl_2$ (22 g, 0.1 mole), methanol (50 ml), 50% aqueous sodium hydroxide solution (24 g, 0.3 mole), ethanolamine (6 g), and copper metal (1 g), was refluxed for 24 hours. The reaction mixture was washed with water to give 10.9 g of water insoluble product, which was analyzed by gas chromatography and shown to be 90% $CHF_2OCF_2CHFCl$. There was no unchanged starting material present.

When this procedure was repeated, but with the use of 75 ml. of methanol rather than 50 ml., the water insoluble product recovered amounted to 10.6 g, which is considered to be an insignificant difference.

EXAMPLE 3

Different Reactant Ether

Example 3A

Small Scale Preparation

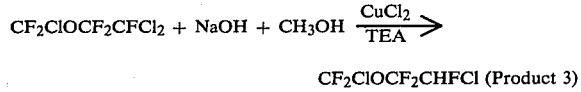

$CF_2ClOCF_2CHFCl$ (Product 3)

A mixture of $CF_2ClOCF_2CFCl_2$ (25.3 g, 0.1 mole), methanol (50 ml), 50% aqueous sodium hydroxide solution (16 g, 0.2 mole), triethanolamine (1 g), and $CuCl_2$ (1 g), was refluxed for nineteen hours. The reaction mixture was poured into water and 19 g of water-insoluble product recovered. This was analyzed by gas chromatography and shown to be about 91% $CF_2ClOCF_2CHFCl$ (Product 3).

Product 3 is useful as a solvent and degreasing agent.

Example 3B

Larger Scale Preparation

This reaction was repeated on a larger scale, and with a more detailed characterization of the product, as follows:

A mixture of $CF_2ClOCF_2CFCl_2$ (253 g, 1 mole), methanol (750 ml), 50% aqueous sodium hydroxide (120 g, 1.5 mole), $CuCl_2$ (10 g), and triethanolamine (10 g), was refluxed for 24 hours. At the end of this time, 85% of the sodium hydroxide had reacted as shown by titration. The reaction mixture was distilled to recover 280 g of product, b.p. 53°–64°, which was washed with water to give 204 g. containing 69% $CF_2ClOCF_2CHFCl$ (Product 3) and 27% unreacted $CF_2ClOCF_2CFCl_2$. This was redistilled to recover in purified form $CF_2ClOCF_2CHFCl$ (Product 3), b.p. 64°, which was identified by its NMR spectrum.

EXAMPLE 4

Different Reactant Ether

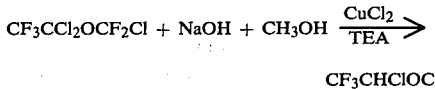

$CF_3CHClOCF_2Cl$ (Product 4)

A mixture of $CF_3CCl_2OCF_2Cl$ (50 g, 0.2 mole), methanol (100 ml), 50% aqueous sodium hydroxide solution (48 g, 0.6 mole), $CuCl_2$ (2 g), and triethanolamine (2 g), was refluxed for five hours. The reaction mixture was washed with water to give 34 g. of water-insoluble product material which was analyzed by gas chromatography and shown to be 79% CF$_3$CHClOCF$_2$Cl (Product 4), which is useful as a solvent and degreasing agent.

In a different run, a reaction mixture of the same composition, after refluxing for 68 hours, produced a major amount of Product 4.

In still another run, a reaction mixture of the same composition except for the sodium hydroxide, which was present in an amount of 24 g. (0.3 mole), produced after 4 hours of reflux a product containing over 90% of Product 4.

EXAMPLE 5

Four Carbon Reactant Ether

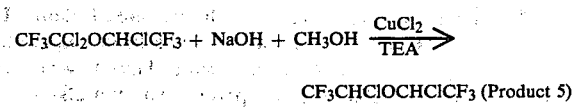

CF$_3$CHClOCHClCF$_3$ (Product 5)

A mixture of CF$_3$CCl$_2$OCHClCF$_3$ (15 g, 0.053 mole), 50% aqueous sodium hydroxide solution (6.4 g, 0.08 mole), methanol (50 ml), CuCl$_2$ (0.1 g), and triethanolamine (0.1 g), was refluxed for four hours and poured into water. The water-insoluble product (10 g) was analyzed by vapor phase chromatography and found to contain 48% CF$_3$CHClOCHClCF$_3$ (Product 5), (dl. form), 38% CF$_3$CHClOCHClCF$_3$ (meso form), and 8% unreacted starting material.

Product 5 is useful as a solvent and degreasing agent.

EXAMPLE 6

Criticality of Ether Reactant

A mixture of CF$_3$CHClOCF$_2$Cl (5.4 g, 0.025 mole), methanol (10 ml.), 50% aqueous sodium hydroxide (4 g., 0.05 mole), CuCl$_2$ (0.25 g), and TEA (0.25 g), was refluxed overnight. The water-insoluble product (2 g) was subjected to NMR spectroscopy. The spectrum showed multipet centered (6 peaks) around 5.8 and two CH$_3$O singlets. None of the expected triplet for —OCHF$_2$ was present. It is concluded that this starting ether does not undergo selective reduction in accordance with the invention.

CONCLUSION

The invention provides a valuable, specific technique for selectively modifying the halogenation of a halogenated aliphatic ether, by a selective reduction process that substitutes a hydrogen substituent for a particular halogen substituent. The process thus makes possible the conversion of hitherto useless halogenated aliphatic ethers to materials that are either useful per se or that can be converted by further processing to directly useful materials.

The invention is of particular value in connection with the production of enflurane anesthetic, since it not only permits the conversion of a major by-product, CHF$_2$OCF$_2$CFCl$_2$, into the desired enflurane anesthetic product, as in Example 2, which is an important advance in the art in and of itself, but it also eliminates the need that previously existed for separating this material from the product stream containing the enflurane (a difficult task because of the many physical and chemical similarities between the compounds and the closeness of their boiling points).

Thus, in the conversion of by-products from the manufacture of enflurane, the "bottoms" are chlorinated to obtain a mixture containing a high proportion of the compound, CHCl$_2$OCF$_2$CFCl$_2$. Fluorination of this compound produces CF$_2$HOCF$_2$CFCl$_2$, which can be reduced by the process of the invention to enflurane, as in Example 2.

The process of this invention has the advantage of being highly specific, in the sense that few unwasted materials appear in the reaction mixture produced. Product recoveries and purifications are thus facilitated and made less expensive. The many useless by-products produced by the presently-employed process are either avoided completely because of the new synthesis tool that is available, or the quantity and number is reduced.

The process provides new ways to synthesize valuable materials and, in addition, provides a way to convert presently useless or unusual halogenated by-products into valuable intermediates.

While the invention has been disclosed herein by reference to the details of preferred embodiments, it is to be understood that the disclosure is intended in an illustrative sense, and it is contemplated that modifications may be made in the process within the spirit of the invention and the scope of the appended claims.

We claim:

1. A process for replacing a halogen substituent with hydrogen in a halogenated aliphatic ether of the methyl-ethyl or ethyl-ethyl type, comprising reacting a primary or secondary alkanol and an inorganic base selected from the group consisting of alkali and alkaline earth metal hydroxides and alkoxides, in the presence of a catalyst selected from the group consisting of copper, silver, cobalt, tin, manganese, nickel, iron, molybdenum, chromium, antimony, vanadium, the salts thereof, an amine, and mixtures thereof, with a halogenated aliphatic ether of the formula:

(a) CX$_3$OCY$_2$CZ$_3$ where

CX$_3$ is CF$_3$, CH$_3$, CH$_2$F, CF$_2$Cl, CF$_2$Br, or CHF$_2$; and

CZ$_3$CY$_2$ is CF$_3$CCl$_2$, CF$_3$CClBr, CF$_3$CBr$_2$, CFCl$_2$CF$_2$, CFCl$_2$CFCl, CFCl$_2$CFBr, CFBrClCF$_2$, CFClBrCFCl, CFBrClCFBr, CCl$_3$CF$_2$, CFBr$_2$CF$_2$, CFBr$_2$CFCl, CFBr$_2$CFBr, CCl$_2$BrCF$_2$, CClBr$_2$CF$_2$ or CBr$_3$CF$_2$, or (b) CX$_3$CY$_2$OCY$_2$CX$_3$ where at least one of the CX$_3$CY$_2$ groups is selected from the following:

CF$_3$CCl$_2$, CF$_3$CClBr, CF$_3$CBr$_2$, CFCl$_2$CF$_2$, CFCl$_2$CFCl, CFCl$_2$CFBr, CFBrClCF$_2$, CFBrClCFCl, CFBrClCFBr, CCl$_3$CF$_2$, CFBr$_2$CF$_2$, CFBr$_2$CFCl, CFBr$_2$CFBr, CCl$_2$BrCF$_2$, CClBr$_2$CF$_2$ or CBr$_3$CF$_2$;

and the other CX$_3$CY$_2$ group may be the same or may be selected from the following:

CF$_3$CH$_2$, CF$_3$CHF, CF$_3$CHCl, CF$_3$CHBr, CF$_3$CF$_2$, CF$_3$CFCl, CF$_3$CFBr, CH$_3$CH$_2$, CHFCH$_2$, CHF$_2$CF$_2$, CFClCF$_2$, CF$_2$ClCFCl, CF$_2$ClCFBr, CF$_2$BrCF$_2$, CF$_2$BrCFCl, CF$_2$BrCFBr, CHFBrCF$_2$, CHCl$_2$CF$_2$, CHClBrCF$_2$, or CHBr$_2$CF$_2$.

2. A process in accordance with claim 1 wherein the aliphatic ether reactant is

CF$_3$CCl$_2$OCHF$_2$ and the reduced ether product is $CF_3CHClOCHF_2$

3. A process in accordance with claim 1 wherein the aliphatic ether reactant is $CFCl_2CF_2OCHF_2$ and the reduced ether product is $CHFClCF_2OCHF_2$.

4. A process in accordance with claim 1 wherein the aliphatic ether reactant is $CFCl_2CF_2OCF_2Cl$ and the reduced ether product is $CHFClCF_2OCF_2Cl$.

5. A process in accordance with claim 1 wherein the aliphatic ether reactant is $CF_3CCl_2OCF_2Cl$ and the reduced ether product is $CF_3CHClOCF_2Cl$.

6. A process in accordance with claim 1 wherein the aliphatic ether reactant is $CF_3CCl_2OCHClCF_3$ and the reduced ether product is $CF_3CHClOCHClCF_3$.

7. A process in accordance with any one of claims 1, 2, 3, 4, 5, or 6, wherein the alkanol is a lower alkanol.

8. The process in accordance with claim 1, wherein said alkali metal alkoxide comprises a sodium alkoxide.

9. A process in accordance with claim 1 or 8 wherein said alkoxide comprises a methoxide.

* * * * *